(12) United States Patent
Nock et al.

(10) Patent No.: US 6,720,165 B2
(45) Date of Patent: Apr. 13, 2004

(54) METHODS FOR MAKING ANTIBODY FRAGMENTS AND COMPOSITIONS RESULTING THEREFROM

(75) Inventors: Steffen Nock, Redwood City, CA (US); David S. Wilson, Hayward, CA (US); Jiangchun Wu, Fremont, CA (US)

(73) Assignee: Zyomix, Inc., Hayward, CA (US)

( * ) Notice: Subject to any disclaimer, the term of this patent is extended or adjusted under 35 U.S.C. 154(b) by 0 days.

(21) Appl. No.: 09/882,814

(22) Filed: Jun. 14, 2001

(65) Prior Publication Data

US 2002/0193573 A1 Dec. 19, 2002

(51) Int. Cl.[7] .................... C07K 16/00; C12P 21/06
(52) U.S. Cl. ................ 435/68.1; 435/70.21; 530/387.1; 530/866
(58) Field of Search .................. 435/68.1, 70.21; 436/512; 530/387.1, 866

(56) References Cited

U.S. PATENT DOCUMENTS

| | | | |
|---|---|---|---|
| 4,849,352 A | 7/1989 | Sullivan et al. | |
| 5,099,005 A | * 3/1992 | Nichols et al. | 530/388.1 |
| 5,585,097 A | 12/1996 | Bolt et al. | |
| 6,218,149 B1 | 4/2001 | Morrison et al. | |
| 2002/0150914 A1 | 10/2002 | Anderson et al. | |

OTHER PUBLICATIONS

Calbiochem Catalog 1994/1995, p. 234.*

* cited by examiner

Primary Examiner—David Saunders
(74) Attorney, Agent, or Firm—Townsend and Townsend and Crew LLP

(57) ABSTRACT

Improved methods for making antibody fragments, preferably F(ab')$_2$ fragments from various classes and subclasses of antibodies is described. Pretreatment of antibodies with deglycosylases or cellular inhibition of glycosylation during expression, yields antibodies having improved susceptibility towards protease cleavage, preferably pepsinolysis, which yields F(ab')$_2$ antibody fragments. Compositions resulting from such methods are further disclosed.

9 Claims, 4 Drawing Sheets

METHODS FOR MAKING ANTIBODY FRAGMENTS AND COMPOSITIONS RESULTING THEREFROM

FIELD OF THE INVENTION

This invention relates to the fields of antibodies and fragments thereof, immunology, biological and chemical assay development, drug discovery, medical diagnostics and treatments, and proteomics.

RELATED REFERENCES

Andrew, S. M, and Titus, J. A. (1997). Purification and Fragmentation of Antibodies. In *Current Protocols in Immunology*, edited by Coligan, J. W., Kruisbeek, A. M., Margulies, D. H., Shevach, E. M. and Strober, W., John Wiley & Sons, N.Y., pp. 2.7.1–2.7.12.

Gorini, G., Medgyesi, G. A. and Doria, G. (1969). Heterogeneity of mouse myeloma gamma-G globulin as revealed by enzymatic proteolysis. J. Immunol. 103, 1132–1142.

Harris, L. J., Larson, S. B., Hasel, K. W. and McPherson, A. (1997). Refined structure of an intact $IgG_{2a}$ monoclonal antibody. Biochemistry 36, 1581–1597.

Hindley, S. A. et al. (1993). The interaction of IgG with Fc-gamma-RII: involvement of the lower hinge binding site as probed by NMR. Biochem. Soc. Trans. 21, 337S.

Kim, H., et al. (1994). O-Glycosylation in hinge region of mouse immunogloblulin $G_{2b}$. J. Biol. Chem. 269, 12345–12350.

Laemmli, U. K. (1970). Cleavage of structural proteins during the assembly of the head of the bacteriophage T4. Nature 227, 680–5.

Lamoyi, E. and Nisonoff, A. (1983). Preparation of $F(ab')_2$ fragments from mouse IgG of various subclasses. J. Immunol. Methods 56, 235–243.

Mariani, M., Cauragra, M., Tarditi, L. and Seccariani, E. (1991). A new enzymatic method to obtain high-yield $F(ab')_2$ suitable for clinical use from mouse $IgG_1$. Mol Immunol. 28, 69–77.

Milenic, D. E., Esteban, J. M., Colcher, D. (1989). Comparison of methods for the generation of immunoreactive fragments of a monoclonal antibody (B72.3) reactive with human carcinomas. J. Immunol. Methods 120, 71–83.

Nisonoff, A, Wissler, F. C., Lipman, L. N. and Woernley, D. L. (1960). Separation of univalent fragments from the bivalent rabbit antibody molecule by reduction of disulfide bonds. Arch. Biochem. Biophys. 89, 230–244.

Parham, P. (1983). On the fragmentation of monoclonal $IgG_1$, $IgG_{2a}$, and $IgG_{2b}$ from BALB/c mice. J. Immunol. 131, 2895–2902.

Parham, P. (1986). Preparation and purification of active fragments from mouse monclonal antibodies. In *Handbook of Experimental Immunology*, Vol. 1: Immunochemistry (D. M. Wier, ed.) pp14.1–14.23. Blackwell Scientific, Oxford.

Rousseaux, J., Rousseaux-Prevost, R. and Bazin, H. (1983). Optimal conditions for the preparation of Fab and $F(ab')_2$ fragments from monoclonal IgG of different rat IgG subclasses. J. Immunol. Methods 64, 141–146.

Yamaguchi, Y., Kim, H., Kato, K., Masuda, K., Shimada, I. and Arata, Y. (1995). Proteolytic fragmentation with high specificity of mouse immunoglobulin G: Mapping of the proteolytic cleavage sites in the hinge region. J. Immunol. Methods 181, 259–267.

BACKGROUND OF THE INVENTION

Antibodies, and in particular, antibody fragments, are heavily utilized in diagnostic, therapeutic, and biological research applications. Often there are substantial advantages to using antibody fragments that are produced by proteolysis of IgGs.

Full size IgG antibodies have three domains, each of approximately 50 kd molecular weight, the three domains comprising two identical "Fab" (antigen binding) fragments, and an Fc (crystallizable domain). It is often advantageous to remove the Fc domain from the antibody prior to use to yield, as in the case of pepsin cleavage, a $F(ab')_2$ fragment separated from the Fc domain. An $F(ab')_2$ maintains the binding characteristics of a full size IgGs despite its loss of the Fc domain. The Fc domain can invoke a variety of undesired biological effector functions that can interfere with the therapeutic or diagnostic uses of the antibodies, thus removal of the Fc region has substantial value. The $F(ab')_2$ is also a useful intermediate in the production of monomeric, chemically tagged Fab monomers because $F(ab')_2$s are held together by 1–3 disulfide bonds between the heavy chains. Mild chemical reduction of such disulfide bonds may result in the formation of monomeric Fab fragments having cysteines available for reacting with chemical labels or reactive surfaces.

Several classes of IgG antibodies exist having differences based on the sequence of the heavy chain. Consequently, different classes have different susceptibilities to proteolysis by pepsin. Mouse-derived monoclonal antibodies include four IgG subclasses: 1, 2a, 2b and 3. Certain, and often important, members of antibody classes 1 and 2b are recalcitrant to yielding $F(ab')_2$ fragments from pepsinolysis treatment. Even if pepsin cleaves such antibodies, it often does not give good yields or yields different non-$F(ab')_2$ products. Thus many important IgGs cannot be efficiently converted to Fab dimers. Because $IgG_1$ class is the most common for monoclonal antibodies used in biotechnology, there is a need for reliable, universal methods for converting whole $IgG_1$ and other pepsin resistant antibodies to intact $F(ab')_2$ antibody fragments.

Methods for the preparation of $F(ab')_2$ fragments by pepsinolysis have been described which produce antibody fragments that retain full binding activity but do not possess the effector functions conferred by the Fc domain. See Nisonoff et al., and Andrew and Titus. However, as discussed herein, these methods are of limited use depending, in part, on the type and source of antibody used as a starting material. $F(ab')_2$ fragments may be selectively reduced to Fab fragments having free cysteines in the linker region (Nisonoff et al.) This allows Fab fragments to be labeled or attached to solid supports or labels through a region of the protein that is distal to the antigen-binding site. The most common method for generating $F(ab')_2$ fragments is by pepsinolysis, which is generally efficient for most antibodies from the mouse $IgG_{2a}$ and $IgG_3$ subclasses, but not generally efficient for those from the $IgG_{2b}$ or $IgG_1$, the latter being the most common.

Many others have reported poor yields of $F(ab')_2$ fragments by treating mouse $IgG_1$ antibodies with pepsin under standard conditions (37° C., pH 4.5), and such procedures typically also produce several other cleavage products as well (See Gorini et al.; Laymoyi and Nisonoff; Parham; Mariani et al.; and, Andrew and Titus.) About 50% of the $IgG_1$ antibodies appeared to be completely resistant to pepsinolysis. Numerous alternatives to pepsinolysis have been described for generating $F(ab')_2$ fragments from $IgG_1$ molecules, including the use of papain (under slightly reducing conditions), V8 protease, or ficin, for example. See generally Parham; Milenic et al.; Mariana et al.; Yamaguchi et al.; and, Andrew and Titus, however, each of these failed to provide a reliable method for preparing F(ab')$_2$s from antibodies with uniform, predictable results. Thus, there is a need for a universal method for preparing F(ab')$_2$ antibody fragments from whole antibodies, especially those from IgG$_1$ and IgG$_{2b}$ subclasses. There is also a need for a method for converting other immunoglobulins from other species such as chickens and their IgY antibodies. The invention disclosed herein addresses these, and other needs as discussed below and as will become apparent to one of ordinary skill in the art reading this disclosure and subsequent claims.

SUMMARY OF THE INVENTION

The invention provides methods for making F(ab')$_2$ antibody fragments from antibodies, in particular, antibodies that have one or more oligosaccharide groups attached to regions of the antibody other than the hinge region.

In one aspect, the invention provides a method for preparing a F(ab')$_2$ fragment from a glycosylated antibody. The method includes the steps of providing a glycosylated antibody where the glycosylated antibody has a hinge region having one or more protease cleavage sites located within the hinge region, and one or more non-hinge regions adjacent the hinge region, the non-hinge region(s) having one or more oligosaccharide groups attached thereto, where the oligosaccharide group(s) cause the protease cleavage site(s) within the hinge region to be resistant to a proteolysis treatment. The glycosylated antibody or antibodies are then exposed to a deglycosylation treatment, the deglycosylation treatment cleaving the oligosaccharide group(s) attached to the non-hinge region(s) to form a partially or wholly deglycosylated antibody having a hinge region cleavable by the proteolysis treatment. The partially or wholly deglycosylated antibody or antibodies are then exposed to the proteolysis treatment to cause proteolytic cleavage of the hinge region cleavable by the proteolysis to form the F(ab')$_2$ fragment.

Certain preferred embodiments may have at least one of the following features such as; the glycosylated antibody being a plurality of glycosylated antibodies, at least some of the glycosylated antibodies being polyclonal, the glycosylated antibodies being monoclonal, the glycosylated antibody being either an IgG$_1$ or IgG$_{2b}$ glycosylated antibody, the IgG$_1$ or IgG$_{2b}$ antibody being from a rodent-derived hybridoma cell culture or ascites, the glycosylated antibody being derived from the group consisting of rat, mouse, rabbit, goat, sheep, lamb, chicken, or horse, the proteolysis being achieved wholly or partly from protease treatments including components selected from the list consisting of pepsin, proteases that cleave pepsin substrates, papain, papain pre-activated with cysteine, and ficin, the proteolysis being achieved by a protease capable of producing F(ab')$_2$ fragments from the deglycosylated antibodies, the deglycosylase treatment containing a glycosidase combination selected from the group consisting of PNGase F, endo-O-glycosylase, sialidase A, PNGase F/endo-O-glycosylase, PNGase F/sialidase A, PNGase F/endo-O-glycosylase/sialidase A, endo-O-glycosylase/sialidase A, and/or the non-hinge regions comprising the Fc and the F(ab') regions of the glycosylated antibody.

Another aspect of the invention provides for a method for preparing F(ab')$_2$ fragments. The method includes the steps of growing a hybridoma cell that normally produces glycosylated antibodies where the glycosylated antibodies have a hinge region with one or more protease cleavage sites located within the hinge region, one or more non-hinge regions adjacent the hinge region, and one or more oligosaccharide groups being attached to at least one of the non-hinge regions by the hybridoma cell through glycosylation, the oligosaccharide groups causing the hinge regions to be resistant to a proteolysis treatment. The hybridoma cell or cells are administered an inhibitor of the glycosylation effective to inhibit glycosylation of the antibodies to produce one or more unglycosylated antibodies lacking the oligosaccharides within at least one non-hinge region to render the hinge region prone to the proteolysis treatment. The unglycosylated antibodies are exposed to the proteolysis treatment so that the unglycosylated antibodies' hinge regions are cleaved to form the F(ab')$_2$ fragments from the unglycosylated antibodies.

Certain preferred embodiments of the invention may include the hybridoma cell being a part of a hybridoma cell culture or ascites, the hybridoma cell being a plurality of hybridoma cells, the hybridoma cell being part of a monoclonal or polyclonal hybridoma cell line, the hybridoma cells being from the same hybridoma cell line, the hybridoma cells being from different hybridoma cell lines, and/or the inhibitor of the glycosylation contains bacitracin or tunicamycin.

Another aspect of the invention provides a method for preparing F(ab')$_2$ fragments. The method includes the steps of providing a hybridoma cell line that normally produces glycosylated antibodies, the glycosylated antibodies having a hinge region with one or more protease cleavage sites located within the hinge region, one or more non-hinge regions adjacent the hinge region, and one or more oligosaccharide groups being attached to at least one of the non-hinge regions by the hybridoma cell through glycosylation, where the oligosaccharide groups cause the hinge regions to be resistant to a proteolysis treatment. The hybridoma cell line or lines are then altered to inhibit glycosylation of the antibodies within the non-hinge regions to produce one or more unglycosylated antibodies such that the unglycosylated antibodies are susceptible to proteolysis treatment and caused to produce the unglycosylated antibodies. The unglycosylated antibodies are then exposed to the proteolysis treatment to cleave the unglycosylated antibodies to produce the F(ab')$_2$ fragments.

Certain preferred embodiments may have the hybridoma cell being part of a hybridoma cell culture or ascites, and/or the altered cells being either permanently or transiently altered.

In another aspect, the invention provides for an F(ab')$_2$ composition comprising: one or more F(ab')$_2$ fragments, or derivative therefrom, produced by a method selected from the methods disclosed above. In certain embodiments, the F(ab')$_2$ fragments are an active ingredient of an anti-toxin or anti-venom medicament.

Yet another aspect of the invention provides for an immunoglobulin composition comprising: one or more aglycosylated or deglycosylated immunoglobulins, the aglycosylated or deglycosylated immunoglobulins being formed by preventing the attachment of one or more oligosaccharides to the immunoglobulin, or effecting the removal of an attached oligosaccharide from the immunoglobulin by exposure to one or more deglycosylases, or both by preventing attachment to and removing one or more oligosaccharides from the immunoglobulin. At least one of the one or more aglycosylated or deglycosylated immunoglobulins becomes cleavable by a protease which cleaves the aglycosylated or deglycosylated immunoglobulins at a position to form F(ab')$_2$ fragment(s) from the aglycosylated or deglycosylated immunoglobulins as a result of the immunoglobulin being aglycosylated or deglycosylated.

Still yet another aspect of the invention provides for a kit for making F(ab')$_2$ fragments from one or more immunoglobulins, at least one of the immunoglobulins having one or more oligosaccharides attached thereto that inhibit protease activity that converts the immunoglobulins into F(ab')$_2$ fragments comprising: a deglycosylation composition containing one or more deglycosylase enzymes capable of removing some or all of the oligosaccharides; and, a protease composition containing one or more proteases capable of reacting with the immunoglobulin produces F(ab')$_2$ fragments from the deglycosylated antibodies. In certain preferred embodiments, the kit further comprises a purification medium for purifying the F(ab')$_2$ fragments from non-F(ab')$_2$ fragments of the immunoglobulin or from uncleaved immunoglobulin, and/or the kit further comprises instructions for carrying out the method selected from the group consisting of the methods disclosed above.

These and other aspects and embodiments thereof of the invention will become apparent to one skilled in the art by way of reading the specification and drawings below.

DETAILED DESCRIPTION OF THE PREFERRED EMBODIMENTS

Figure 1:
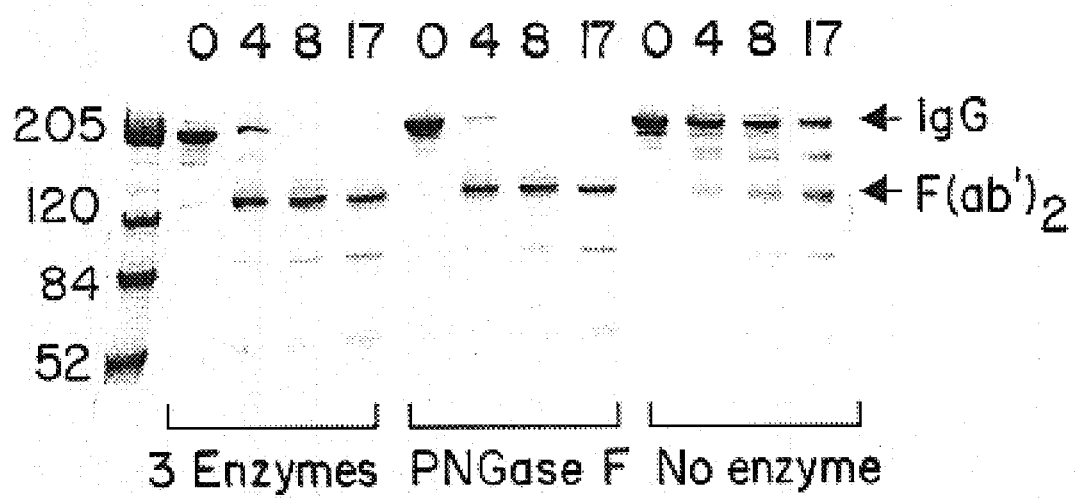
FIG. 1 depicts a gel image demonstrating how deglycosylation improves pepsinolysis of IgG$_1$ conversion to F(ab')$_2$ fragments.

The term "antibody" means one or more antibodies. Included in the term antibodies are immunoglobulins, whether natural or partially or wholly produced artificially, e.g. recombinant. An antibody may be monoclonal or polyclonal. The antibody may, in some cases, be a member of one, or a combination immunoglobulin classes, including: IgG, IgM, IgA, IgD, and IgE. Derivatives of the IgG class, however, are preferred in the present invention such as IgG$_1$ and IgG$_{2b}$ subclasses. The present invention contemplates, in some preferred embodiments, providing methods for making immunoglobulins, without regard to origin, cleavable by pepsin or pepsin-like treatments resulting in F(ab')$_2$ fragments, where such immunoglobulins are otherwise not cleavable by pepsin or pepsin-like treatments to yield F(ab')$_2$ fragments. For example, chicken immunoglobulins, IgY, may be made cleavable by pepsin or pepsin-like treatments when subjected to the methods of the present invention to produce F(ab')$_2$ fragments therefrom.

The term "antibody fragment" refers to one or more derivatives of an antibody that is less than full-length. Preferably, the antibody fragment retains at least a significant portion of the full-length antibody's specific binding ability. Examples of antibody fragments include in certain circumstances, but are not limited to Fabs and F(ab')$_2$s.

A "F(ab')$_2$" fragment is an antibody fragment, for example, one essentially equivalent to that obtained from certain pepsin cleavable immunoglobulins (typically IgG) by digestion with pepsin at about pH 4.0–4.5.

A "Fab'" fragment is an antibody fragment essentially equivalent to that obtained by reduction of the disulfide bridge or bridges joining the two heavy chain pieces in the F(ab')$_2$ fragment.

An "Fab" fragment may be an antibody fragment essentially equivalent to that obtained by digestion of immunoglobulins (typically IgG) with the enzyme papain.

A protease is an enzyme capable of cleaving a protein substrate into smaller polymeric or even in some instances, monomeric units. Papain and pepsin are but two examples of proteases. Of particular importance to the present invention are proteases that act on substrates similar to those of the substrates for various forms of pepsin because pepsin, in certain situations, cleaves certain antibodies in a manner that produces highly useful F(ab')$_2$ antibody fragments. The present invention contemplates that other proteases may also produce F(ab')$_2$ fragments from certain whole antibodies in a manner different than that of pepsin, but like pepsin, are affected by the presence of oligosaccharides adjacent the protease substrate site which yields F(ab')$_2$ antibody fragments. In certain embodiments, the protease used is a protease capable of producing F(ab')$_2$ fragments from wholly, or partially deglycosylated antibodies, preferably an antibody whose N-glycosyl attached oligosaccharides are wholly or partially removed.

Pepsinolysis is the activity of cleaving a protein with pepsin or a pepsin-like treatment to produce two or more sub-components from the protein. With respect to antibodies, pepsinolysis yields in certain circumstances, F(ab')$_2$ fragments. Pepsin-like treatment contemplates that other proteases or protease-like processes, whether enzymatic, catalytic, including use of catalytic antibodies, or chemical in nature, which may or may not act on the same substrate or in the same manner as pepsin, may also produce F(ab')$_2$ fragments from certain antibodies and may also benefit from the methods of deglycosylation or aglycosylation described herein.

Glycosidases are, in some embodiments, enzymes that catalyze the hydrolysis of N-glycosidic or O-glycosidic linkages between sugar units, or between sugars and non-sugar units such as amino acids, including amino acids such as asparagine, serine, and threonine, in polypeptides, and in particular in antibodies. A particularly preferred example of a glycosidase is peptide: N-glycosidase (PNGase F) that cleaves the sugar from an asparagine sidechain, leaving aspartic acid. Other embodiments employ different glycosidases that cleave one or more saccharides from certain other amino acids. Yet other embodiments provide that some or all of the attached saccharides are partly or completely degraded resulting in partially or completely deglycosylated antibodies, where such antibodies become cleavable by pepsin or pepsin-like treatments which then result in the production of F(ab')$_2$ fragments. Glycosidases may, for example, include exoglycosylases, endoglycosylases, combinations of exoglycosylase(s) and endoglycosylase(s), and/or may include sialidases, fucosidases, mannosidases, galactosidases, and xylosidases, for example.

Deglycosylation means, in certain embodiments, the removal of one or more attached oligosaccharides from a protein, and in particular, antibody, structure. Deglycosylation may be achieved by enzymatic treatment, including natural or recombinant enzymes in natural, concentrated, or purified forms. Deglycosylation may occur within the antibody cells during growth of the antibodies, or may occur outside such cells during growth by glycosidases produced by such cells or different cells or from enzymes added to the growth media. Deglycosylation may also be achieved by certain chemical procedures or catalytic procedures, including catalytic antibodies, provided such methods do not destroy the binding abilities of the resulting F(ab')$_2$ fragments. Deglycosylation may be complete, partial, or a combination of both, such that the resulting antibody or antibodies become cleavable by pepsin or pepsin-like treatments as a result of such deglycosylation. Deglycosylation treatments may be combined with other strategies, such as aglycosylation, described below, to work in concert to make antibodies become cleavable by pepsin or pepsin-like treatments to produce F(ab')$_2$s.

Aglycosylation means the interruption or prevention of processes that would otherwise produce proteins, and in particular, antibodies, that are glycosylated at one or more position within such proteins or antibodies. This includes processes that reduce the size or amount of branching, or otherwise alter the composition of the glycosylation sites on proteins so as to render them more susceptible to proteolysis by pepsin or to other pepsin-like treatments. Such interruption may arise by exposure to glycosylation inhibitors such as with bacitracin or tunicamycin, or by genetic inhibition of glycosylation including knock-out mutants of such glycosylases or other upstream metabolic components.

Oligosaccharides are typically polymeric sugar molecules, including monomeric sugars, and in some instances containing one or more interrupting monomeric units that are not sugars. Oligosaccharides may include other substitutions attached thereto. The term oligosaccharide, in certain embodiments, is interchangeable with the term carbohydrate which includes monomeric, and/or polymeric carbohydrates. In certain embodiments, antibodies have a conserved glycosylation site, for example on mammalian IgGs in the Fc region (CH$_2$ domain) is at a single asparagine (Asn 297 according to the numbering system used in Edelman et al, Proc. Natl. Acad. Sci. USA 63:78–85, 1969.) The invention provides removing oligosaccharides from antibodies at conserved, preferably known conserved, positions within the antibody.

Hybridomas are cells made from, for example, non-antibody-secreting cultured myeloma cells with normal B cells from the spleen of an immunized mouse. The fusion of a myeloma cell from a line that has lost the ability to secrete immunoglobulin with a B cell known to secrete a particular antibody results in a remarkable hybrid cell that produces the antibody made by its B-cell component but retains the capacity of its myeloma component to multiply indefinitely.

General methods employed by the present invention may be found, for example, in Current Protocols in Immunology (1997), John Wiley & Sons, Inc., herein incorporated by reference in its entirety for all purposes, and for the purpose of providing general methods employed by the present invention.

One aspect of the invention provides for methods for overcoming problems associated with converting mouse IgG molecules, and most importantly IgG$_1$ and IgG$_{2b}$ antibodies, to dimeric Fab fragments. In one embodiment, the invention provides for treating the IgG molecules with reagent(s) that remove N-linked or O-linked oligosaccharides from the IgGs before pepsinolysis to produce deglycosylated antibodies that are more susceptible to cleavage by pepsin to form the dimeric Fab fragment. Deglycosylation improves the pepsinolysis of, for example, important classes of mouse IgGs such as the pepsin-resistant IgG$_1$s and some pepsin-resistant IgG$_{2b}$s.

In preferred embodiments, treating IgGs with commercially available peptide: N-glycosidase (PNGase F) is sufficient to convert the IgGs to a form readily cleavable by pepsin or other F(ab')$_2$ protease to produce F(ab')$_2$ fragments. There are a variety of other methods, including chemical or enzymatic methods that could also be used either to remove the carbohydrate groups, or to deplete glycosylated antibodies from mixtures of glycosylated and non-glycosylated antibody populations. The invention covers any such methods for removing oligosaccharides from antibodies or preventing glycosylation, but in particular, the use of PNGase F or other enzymes to remove the relevant carbohydrate groups is particularly preferred.

According to certain preferred embodiments of the invention, IgG$_1$ molecules are rendered pepsin-sensitive by treatment with peptide: N-glycosidase F (PNGase F), or other enzymes capable of removing N-linked oligosaccharides. The invention provides methods for converting mouse IgG$_1$ antibodies resistant to pepsinolysis absent deglycosylation or aglycosylation treatment to a form that is efficiently cleaved by pepsin under standard reaction conditions. Other embodiments provide for the removal of oligosaccharides, preferably N-linked carbohydrate groups, from IgG$_{2b}$ molecules which are otherwise resistant to pepsinolysis or other F(ab')$_2$-producing protease treatments to increase the yield of F(ab')$_2$ fragments.

This invention describes a method for overcoming the problems associated with converting mouse IgG molecules, and most importantly IgG$_1$ and IgG$_{2b}$ antibodies, to dimeric Fab fragments. The invention provides in certain, preferred embodiments, methods for pre-treating IgG molecules with reagent(s) that remove N-linked oligosaccharides from the IgGs. The resulting deglycosylated antibodies are more susceptible to cleavage by pepsin to form the dimeric Fab fragment. Such deglycosylation improves the pepsinolysis of at certain members of at least two classes of mouse IgGs—IgG$_1$ and IgG$_{2b}$.

In particularly preferred embodiments, treating IgGs with commercially available peptide: N-glycosidase (PNGase F) converts IgGs to readily pepsinolysis cleavable molecules which yield F(ab')$_2$ fragments. There are a variety of other methods, chemical or enzymatic, that could also be used either to remove the carbohydrate groups, or to deplete glycosylated antibodies from mixtures of glycosylated and non-glycosylated antibody populations.

Another aspect of the invention provides for kits for making F(ab')$_2$ fragments from one or more immunoglobulins, at least one of the immunoglobulins having one or more oligosaccharides attached thereto that inhibit protease activity that converts the immunoglobulins into F(ab')$_2$ fragments comprising: a deglycosylation composition containing one or more deglycosylase enzymes or chemicals capable of removing or reducing some or all of the oligosaccharides; and, a protease composition containing one or more proteases capable of reacting with the immunoglobulin produces F(ab')$_2$ fragments from the deglycosylated antibodies. In preferred embodiments, the kit further comprises a purification medium for purifying the F(ab')$_2$ fragments from non-F(ab')$_2$ fragments of the immunoglobulin or from uncleaved immunoglobulin, and/or further comprising instructions for carrying out the method selected from the group consisting of the methods disclosed above.

The invention further provides for medicaments which employ as active ingredients, F(ab')$_2$ fragments, such medicaments including, for example, anti-toxin remedies and anti-venom remedies.

The invention, in another aspect, provides for intermediate stage immunoglobulins, preferably antibodies, which have been partially or wholly deglycosylated, aglycosylated, or both, to make such immunoglobulins cleavable by an F(ab')$_2$ producing protease to form F(ab')$_2$ fragments from such immunoglobulins.

All references cited herein are incorporated by reference in their entirety for all purposes and any stated purpose as if each reference were incorporated by reference in its entirety as such where individually cited.

EXAMPLES

Antibodies

MAB9647 (raised against human IL-8) was produced by Covance, Inc. (Princeton, N.J.) from mouse ascites fluid using the hybridoma cell line HB-9647 from ATCC (Manassas, Va.) and was protein G-purified. MAB3.1 was raised against human IL-3 by BD Pharmingen (Franklin Lakes, N.J.) and was protein G-purified from tissue culture supernatent. MAB206 was raised against human IL-6 by R&D Systems (Minneapolis, Minn.) and was protein A-purified from mouse ascites fluid from clone 6708.111 (catalog number MAB206). MAB6002 raised against the human IgG Fc region was produced by Covance, and obtained from mouse ascites fluid using the hybridoma cell line CRL-1788 from ATCC and was protein G-purified. MAB 6001 raised against the human IgG1 Fc region was produced by Covance from mouse ascites fluid using the hybridoma cell line CRL-1755 from ATCC and was protein G-purified.

Antibody Deglycosylation

Individual glycosidases or combinations thereof, were prepared as follows: 50 U/ml PNGase F alone, and a combination of 50 U/ml PNGase F with 0.012 U/ml endo-o-glycosylase, and 0.05 U/ml Sialidase A. (Enzymes were obtained from Prozyme of San Leandro, Calif. or New England Biolabs, Beverly, Mass. In the above situations, the Prozyme unit definitions are used. For all cases below for the PNGase, the unit definition was established by New England Biolabs.) Reaction cocktails contained 1 mg/ml IgG in a 50 mM Na$_2$PO$_4$, pH 7.0 buffer, and were reacted at about 37° C. for 36 hours. Deglycosylation treatments may also be carried out using 1–4 mg/ml antibody in 50 mM NaPO$_4$, pH of about 7.5, and 10–20 U/μl PNGase F. PNGase F is purified from *Flavobacterium meningosepticum* and has an apparent molecular weight of about 36,000 Daltons. PNGase F cleaves between the innermost GlcNAc and asparagine residues of high mannose, hybrid, and complex oligosaccharides from N-linked glycoproteins. One unit of PNGase is defined by New England Biolabs as being the amount of enzyme required to remove >95% of the carbohydrate from 10 μg of denatured RNase B in 1 hour at 37° C. in a total reaction volume of 10 μl (65 NEB units=1 IUB milliunit).

Endo-O-glycosidase (O-glycopeptide endo-D-galactosyl-N-acetyl-alpha-galactosaminohydrolase, EC 3.2.1.97) cleaves unsubstituted Galbeta(1–3)GalNAcalpha disaccharides attached to the serine or threonine residues of glycoproteins or glycopeptides. Substitutions such as sialic acid, galactose, fucose or N-acetylglucosamine may first be removed with the appropriate exoglycosidase prior to treatment with Endo-O-Glycosidase. Typically, a neuraminidase such as Sialidase A is used to remove sialic acid. One unit of Endo-O-Glycosidase is defined as the amount of enzyme required to produce 1 umole of p-nitrophenol in 1 min at 37° C. pH 5 from -nitrophenyl-2-acetamido-2-deoxy-3-O-(beta-D-galactopyranosyl)-alpha-D-galactopyranoside. Sialidase A (N-acetylneuraminate glycohydrolase, EC 3.2.1.18) cleaves all non-reducing terminal sialic acid residues from complex carbohydrates and glycoproteins. The relative cleavage rates for different linkages are: alpha(2–6)>alpha(2–3)>alpha(2–8), alpha(2–9). In addition, Sialidase A will cleave branched sialic acids (linked to an internal residue). This property makes it unique among sialidases. High concentrations of enzymes and prolonged incubation times may be required for cleaving branched residues. One unit of Sialidase A is defined as the amount of enzyme required to produce 1 μmole of methylumbelliferone in 1 minute at 37° C. pH 5 from 2'-(4-methylumbelliferyl)-alpa-D-N-actylneuraminic acid.

Pepsinolysis

After carrying out deglycosylation reactions, antibodies are buffer-exchanged into 20 mM NaOAc, pH 4.5. PNGase was optionally present during pepsinolysis. Pepsinolysis conditions were 30% v/v pepsin agarose (settled bed volume, beads washed in 20 mM NaOAc, pH 4.5), about 0.5 to 2 mg/ml IgG, 20 mM NaOAc, 260 mM KCl, 0.1% Triton-X-100, pH 4.5. Reactions were incubated at 37° C. with agitation for stated periods of time. After each time point, the slurry was loaded onto a centrifugal filter device (Millipore UFC30HVNB, Bedford, Mass.) and spun in a microcentrifuge (12,000 g for 2 minutes). The resulting filtrate was diluted 1:1 with non-reducing protein loading buffer (62.5 mM Tris HCL, 25% glycerol, 2% SDS, 0.01% Bromphenol Blue) and loaded onto a 4–20% gradient SDS-polyacrylamide gel (Product number 161–1123, Bio Rad, Hercules, Calif.). SDS-PAGE was performed according to Laemmli (1970).

F(ab')$_2$ Reduction and Alkylation

The products of the pepsin cleavage were exchanged by dialysis into 0.1M Na$_2$PO$_4$, 5 mM EDTA, pH 6.0, and then treated with 20 mM 2-mercaptoethylamine (MEA) for 90 minutes at 37° C. The MEA was then removed by dialyzing for 6 hours at 4° C. against 0.1 M Na$_2$PO$_4$, 5 mMEDTA, pH 6.0, using a Sephadex G-25 column (PD-10, Amersham-Pharmacia, Piscataway, N.J.). The reduced Fab' was then treated with 20 mM maleimide-activated biotin (Pierce product No. 21901) or N-ethylmaleimide (NEM) for 2 hours at room temperature, and the unincorporated biotin-maleimide or NEM was then removed by gel filtration (Superdex-75 resin, Amersham-Pharmacia). Antigen-binding activity of the biotinylated F(ab') fragments was confirmed by Surface Plasmon Resonance (SPR) using streptavidin-coated chips (Biocore 3000, Uppsala, Sweden).

Streamlined Deglycosylation/Pepsinolysis

A preferred method for producing F(ab')$_2$ fragments includes the following steps. Antibodies (1–4 mg/ml) in 25 mM Na$_2$PO$_4$, pH 7.5 is treated with 5U/μl PNGase F (New England BioLabs unit definition and reagent) for 4 or more hours. Pepsinolysis is then carried out using a pepsinolysis reaction containing 30% by volume pepsin agarose beads (volume of settled matrix bed, washed in 20 mM NaOAc, pH 4.5), 20% by volume 5x pepsinolysis buffer (163 mM NaOAc, 1M KCl, 0.5% Triton-X-100, pH 3.5) and 50% by volume of the abovementioned deglycosylation reaction. Hence, there is no need for buffer exchange or PNGase F removal. The resulting cocktail typically has a pH of about 4.5. The pepsinolysis is carried out for about 1–14 hours, depending on which antibody is used. Eight hours is usually optimal.

Data

FIG. 1 depicts a gel image demonstrating how deglycosylation improves pepsinolysis of $IgG_1$ conversion to $F(ab')_2$ fragments. A 17 hour time-course of MAB9647 after treatment with a cocktail of three enzymes that remove both N- and O-linked carbohydrate groups ("3 Enzymes"), or that remove only N-linked carbohydrates ("PNGase F"), or a control reaction with no glycosidase. The positions of fill length IgG and the $F(ab')_2$ fragments are shown. The number of hours of pepsinolysis is shown at the top of each lane.

Figure 2:
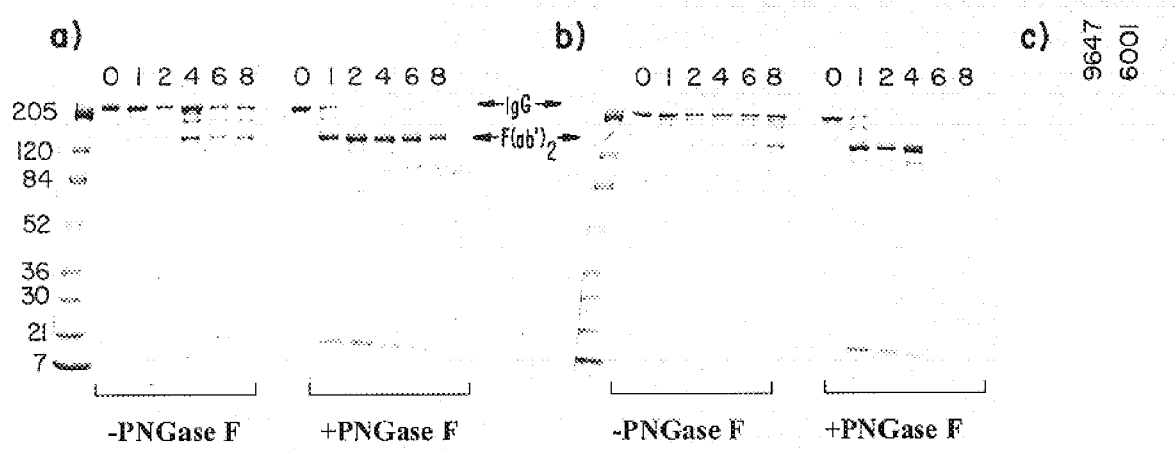
FIG. 2 depicts a time-course of pepsinolysis of IgG$_1$ and IgG$_{2b}$ subclasses.

FIG. 2 depicts a time-course of pepsinolysis of $IgG_1$ and $IgG_{2b}$ subclasses. The time (in hours) of pepsin-treatment is shown at the top of each lane, after treatment with PNGase F or a control reaction with no glycosidase. Panel (a) demonstrates the behavior of MAB947, an $IgG_1$ subclass antibody, and panel (b) shows a similar result for MAB6001, of subclass $IgG_{2b}$. Panel (c) shows the result of converting the $F(ab')_2$ fragments from MAB9647 and MAB6001 into monomeric Fab' fragments by treatment with 2-mercaptoethylamine followed by alkylation with N-ethylmaleimide.

Figure 3:
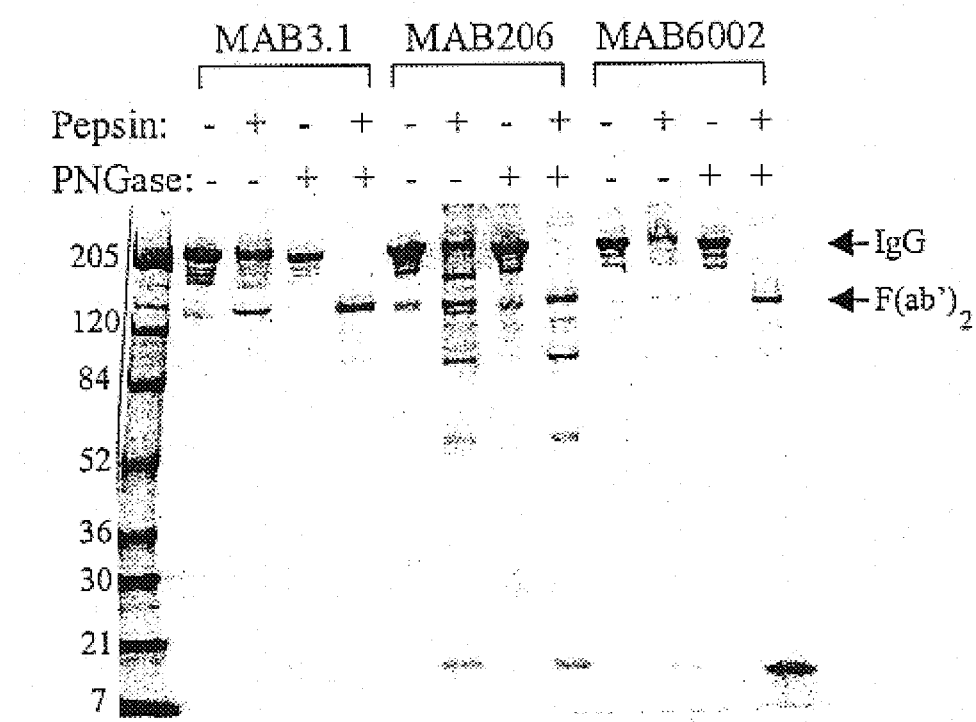
FIG. 3 depicts further examples of the effect of PNGase F-treatment on the pepsinolysis of IgG$_1$ antibodies.

FIG. 3 depicts further examples of the effect of PNGase F-treatment on the pepsinolysis of $IgG_1$ antibodies. Three IgG molecules were either treated with PNGase F or no glycosidase, and then exposed to pepsin for various times (MAB3.1: 8 hours; MAB206: 10 hours; and MAB6002: 5 hours).

Figure 4:
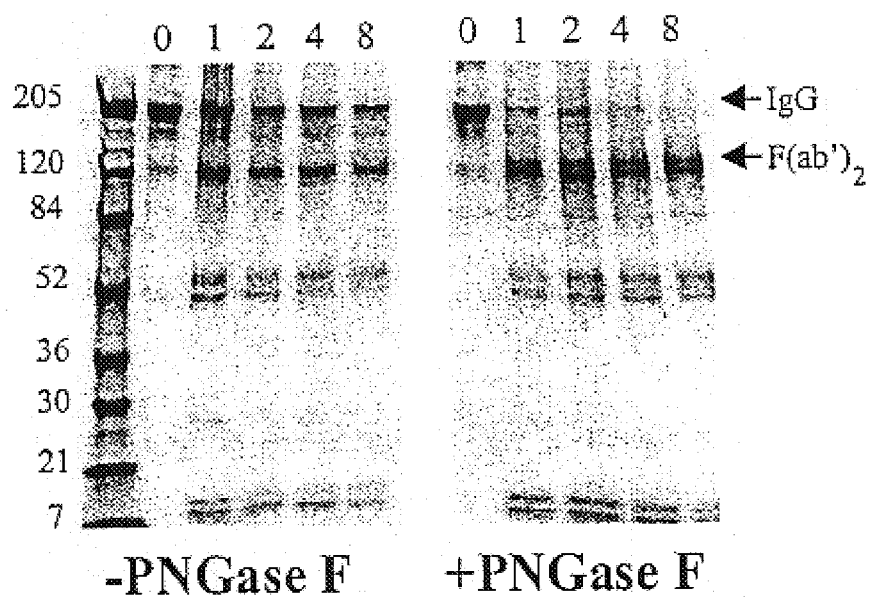
FIG. 4 depicts results from treatment of a polyclonal IgG population from a non-immunized mouse with PNGase F, followed by a pepsinolysis time-course.
Figure 5:
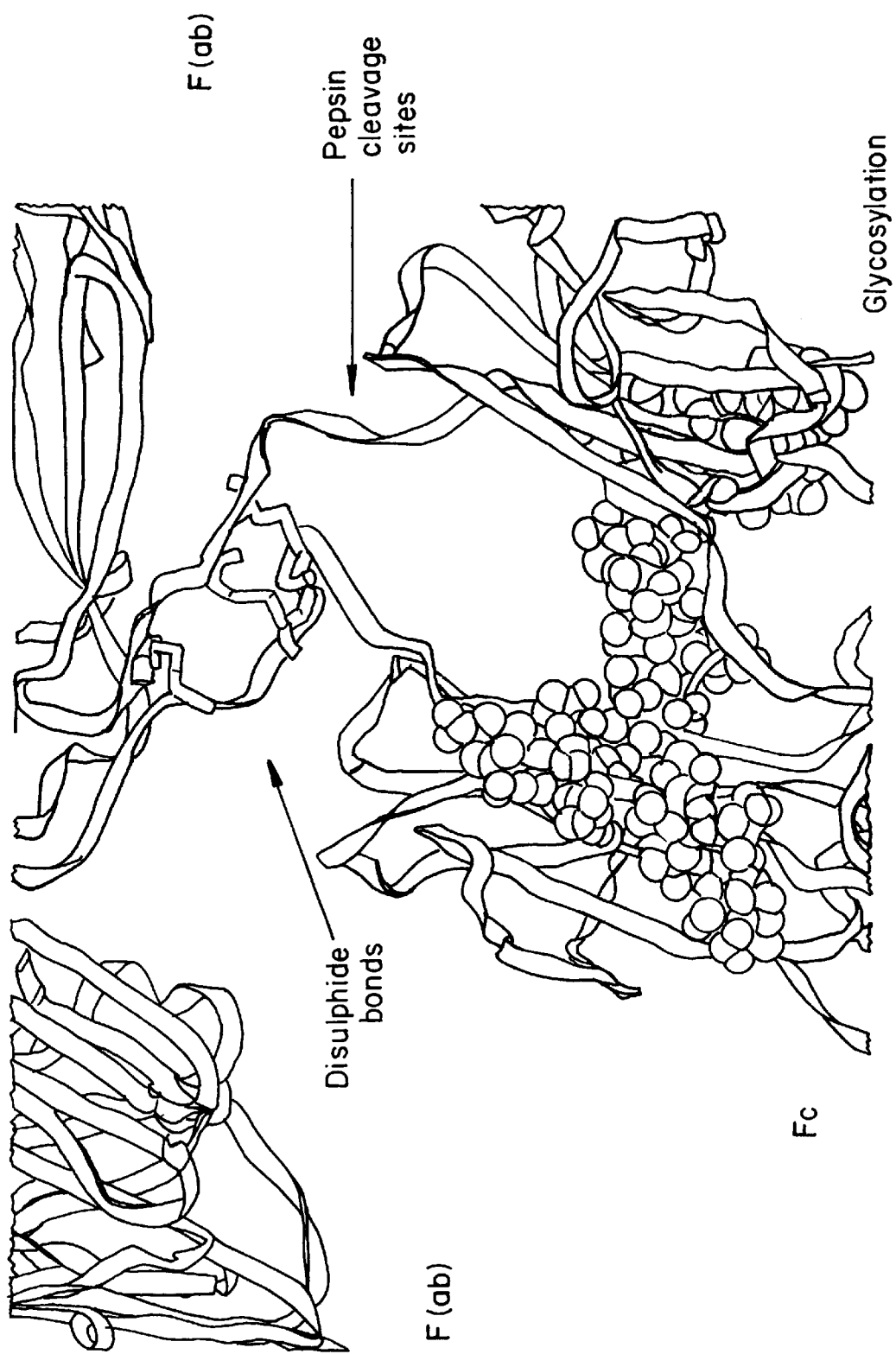
FIG. 5 shows the structure of an immunoglobulin hinge region.

FIG. 4 depicts results from treatment of a polyclonal IgG population from a non-immunized mouse with PNGase F, followed by a pepsinolysis time-course. The time in hours is shown above each lane.

What is claimed is:

1. A method for preparing a $F(ab')_2$ fragment from a glycosylated antibody, said method comprising the steps of:
   (i) providing said glycosylated antibody, said glycosylated antibody comprising a hinge region, said hinge region comprising one or more protease cleavage sites located within said hinge region and one or more non-hinge regions adjacent to said hinge region, said non-hinge region(s) having one or more oligosaccharide groups attached thereto, said oligosaccharide group(s) causing said protease cleavage site(s) within said hinge region to be resistant to a protease treatment;
   (ii) exposing said glycosylated antibody to a deglycosylation composition thereby cleaving said oligosaccharide group(s) attached to said non-hinge region(s) to form a partially or wholly deglycosylated antibody having a hinge region cleavable by said protease treatment, said deglycosylation composition comprising at least one glycosidase capable of catalyzing the hydrolysis of an N-glvcosidic or O-glycosidic linkage between a sugar unit and an amino acid; and,
   (iii) exposing said partially or wholly deglycosylated antibody to said protease treatment to cause proteolytic cleavage of said hinge region cleavable by said protease treatment to form said $F(ab')_2$ fragment.

2. The method of claim 1 wherein said glycosylated antibody is a plurality of glycosylated antibodies.

3. The method of claim 2 wherein at least some of said glycosylated antibodies are polyclonal.

4. The method of claim 2 wherein said glycosylated antibodies are monoclonal.

5. The method of claim 1 wherein said glycosylated antibody is either an $IgG_1$ or $IgG_{2b}$ glycosylated antibody.

6. The method of claim 5 wherein said $IgG_1$ or $IgG_{2b}$ antibody is from a rodent derived hybridoma cell culture or ascites.

7. The method of claim 1 wherein said glycosylated antibody is derived from the group consisting of rat, mouse, rabbit, goat, sheep, lamb, chicken, or horse.

8. The method of claim 1 wherein said protease treatment comprises contacting said antibody with a protease composition comprising a protease selected from the group consisting of pepsin, proteases that cleave pepsin substrates, papain, papain preactivated with cysteine, and ficin.

9. The method of claim 1 wherein said protease is capable of producing $F(ab')_2$ fragments from said deglycosylated antibodies.

* * * * *

UNITED STATES PATENT AND TRADEMARK OFFICE
CERTIFICATE OF CORRECTION

PATENT NO. : 6,720,165 B2
DATED : April 13, 2004
INVENTOR(S) : Nuck et al.

It is certified that error appears in the above-identified patent and that said Letters Patent is hereby corrected as shown below:

Column 12,
Line 14, replace "N-glvcosidic" with -- N-glycosidic --.

Signed and Sealed this

Seventeenth Day of August, 2004

JON W. DUDAS
*Acting Director of the United States Patent and Trademark Office*